United States Patent
Neigel

(10) Patent No.: US 9,744,120 B2
(45) Date of Patent: Aug. 29, 2017

(54) DURABLE SKIN SANITIZERS CONTAINING WATER STABLE ANTIMICROBIAL SILANOL QUATERNARY AMMONIUM COMPOUNDS

(71) Applicant: Dennis Victor Neigel, Salisbury, NC (US)

(72) Inventor: Dennis Victor Neigel, Salisbury, NC (US)

(73) Assignee: Indusco, Ltd., Greensboro, NC (US)

( * ) Notice: Subject to any disclaimer, the term of this patent is extended or adjusted under 35 U.S.C. 154(b) by 0 days.

(21) Appl. No.: 14/724,364

(22) Filed: May 28, 2015

(65) Prior Publication Data

US 2016/0346193 A1  Dec. 1, 2016

(51) Int. Cl.
| A61K 8/97 | (2017.01) |
| A61K 8/06 | (2006.01) |
| A61Q 17/00 | (2006.01) |
| A61K 8/58 | (2006.01) |
| A61K 8/92 | (2006.01) |

(52) U.S. Cl.
CPC ............... *A61K 8/97* (2013.01); *A61K 8/068* (2013.01); *A61K 8/585* (2013.01); *A61K 8/922* (2013.01); *A61Q 17/005* (2013.01); *A61K 2800/52* (2013.01)

(58) Field of Classification Search
None
See application file for complete search history.

(56) References Cited

U.S. PATENT DOCUMENTS

| 3,560,385 A | 2/1971 | Roth |
| 3,730,701 A | 5/1973 | Isquith et al. |
| 3,794,736 A | 2/1974 | Abbott et al. |
| 3,817,739 A | 6/1974 | Abbott et al. |
| 3,860,709 A | 1/1975 | Abbott et al. |
| 3,865,728 A | 2/1975 | Abbott et al. |
| 4,005,025 A | 1/1977 | Kinstedt |
| 4,005,028 A | 1/1977 | Heckert et al. |
| 4,005,030 A | 1/1977 | Heckert et al. |
| 4,161,518 A | 7/1979 | Wen et al. |
| 4,282,366 A | 8/1981 | Eudy |
| 4,394,378 A | 7/1983 | Klein |
| 4,406,892 A | 9/1983 | Eudy |
| 4,421,796 A | 12/1983 | Burril et al. |
| 4,467,013 A | 8/1984 | Baldwin |
| 4,564,456 A | 1/1986 | Homan |
| 4,567,039 A | 1/1986 | Stadnick et al. |
| 4,615,882 A | 10/1986 | Stockel et al. |
| 4,682,992 A | 7/1987 | Fuchs |
| 4,781,974 A | 11/1988 | Bouchette et al. |
| 4,842,766 A | 6/1989 | Blehm et al. |
| 4,847,088 A | 7/1989 | Blank |
| 4,908,355 A | 3/1990 | Gettings et al. |
| 5,013,459 A | 5/1991 | Gettings et al. |
| 5,411,585 A | 5/1995 | Avery et al. |
| 5,954,869 A | 9/1999 | Elfersy et al. |
| 5,959,014 A | 9/1999 | Liebeskind |
| 6,376,696 B1 | 4/2002 | Raab et al. |
| 6,451,755 B1 | 9/2002 | Norman |
| 6,613,755 B2 | 9/2003 | Peterson et al. |
| 6,632,805 B1 | 10/2003 | Liebeskind |
| 9,089,138 B2 | 7/2015 | Higgins et al. |
| 2005/0008613 A1 | 1/2005 | Peterson et al. |
| 2006/0193816 A1 | 8/2006 | Elfersy et al. |
| 2007/0021383 A1 | 1/2007 | Loder |
| 2007/0237901 A1 | 10/2007 | Moses et al. |
| 2008/0181862 A1 | 7/2008 | Chisholm et al. |
| 2010/0028462 A1 | 2/2010 | Bolkan et al. |

FOREIGN PATENT DOCUMENTS

| GB | 1386876 | 3/1975 |
| WO | WO9741729 | 11/1997 |
| WO | WO0078770 | 12/2000 |
| WO | WO2011123623 | 10/2011 |
| WO | WO2011123623 | 11/2011 |

*Primary Examiner* — Heidi Reese
(74) *Attorney, Agent, or Firm* — Tuggle Duggins P.A.; Blake Hurt

(57) ABSTRACT

This invention is a method of eliminating the number of microorganisms on the surface of skin, hair or nails, by contacting these surfaces with a water stable, antimicrobial silanol quaternary ammonium compounds (SQACs) and the trisilanol, polysiloxanol and water soluble polysiloxane derivatives thereof. The stabilizing agent is selected from a list of volatile, antimicrobial, naturally occurring, renewable phytochemical essential oils and extracts that easily form crystal clear microemulsions when water is added to the concentrated SQAC/essential oil mixture. These non-foaming oil in water microemulsions have excellent long term storage stability, are freeze/thaw stable, remain very low in viscosity and do not phase separate or precipitate for many months. Many of the essential oils found to be useful in this process are non-toxic food additives and have pleasant scents, have low flammability yet are volatile enough to evaporate upon cure down of the SQAC, thereby resulting in a higher concentration of SQAC in the cured, antimicrobial film. Economically shippable concentrations of the stabilized SQACs can be further diluted with water to application concentrations without loosing any of their stabilizing properties and remain storage stable at these lower concentrations indefinitely. In particular, the invention relates to the use of such viscosity controlled aqueous dilutions cured as durable antimicrobial coatings for human or animal skin that covalently bond to the skin, remain active through many washings and reduce or eliminate bacteria, viruses and fungi for days.

12 Claims, No Drawings

DURABLE SKIN SANITIZERS CONTAINING WATER STABLE ANTIMICROBIAL SILANOL QUATERNARY AMMONIUM COMPOUNDS

STATEMENT REGARDING FEDERALLY SPONSORED RESEARCH OR DEVELOPMENT

Not Applicable

REFERENCE TO SEQUENCE LISTING, A TABLE OR A COMPUTER PROGRAM LISTING COMPACT DISK APPENDIX OR A DESCRIPTION OF DRAWINGS

Not applicable

TECHNICAL FIELD OF THE INVENTION

The present invention relates to silanol quaternary ammonium compounds (SQACs) and a process for controlling the viscosity stability of aqueous dilutions of SQACs using naturally derived, renewable phytochemical, essential oils or extracts. In particular, the invention relates to the use of such viscosity controlled aqueous dilutions as antimicrobial agents used to protect human skin, hair and nails from microbial growth.

BACKGROUND OF THE INVENTION

A biocide is any substance that kills microorganisms such as bacteria, molds, algae, fungi or viruses. A biostatic is any substance that inhibits the growth of these organisms. The collective group is called antimicrobials. People have been utilizing antimicrobials, commonly called preservatives, since they first discovered a need to extend the useful life of their food as well as their possessions. Sea salt may have been the first antimicrobial used to preserve food. The mummification techniques employed by early Egyptians used to preserve the human and animal body used salts and a variety of resins. These preservatives were thought to possess magical powers, as well as the ability to install qualities of eternal life.

The existence of microorganisms in nature was discovered in the late 1600s with the invention of the microscope. As early as 1705, mercuric chloride was used to preserve ships' planking against shipworm. It was not until the 19th century discoveries by Pasteur, Gram and others that the causative agents of microbiological deterioration were understood, although use of antimicrobials in a cause and effect relationship with microorganisms is less than a century old.

It is well known in the art that certain slanol quaternary ammonium compounds possess bacteriostatic, fungistatic and algaestatic and/or bactericidal, fungicidal and algaecidal properties. See, for example, U.S. Pat. Nos. 3,730,701; 3,817,739; and 4,394,378; and British Patent No. 1,386,876. For example, one such compound, 3-(trimethoxysilyl)propyl octadecyldimethyl ammonium chloride is a commercial antimicrobial product marketed by Dow Corning as "Bioguard Q 9-5700" (EPA No. 34292-1). U.S. Pat. No. 3,794,736 describes a number of other organoslicon amines and salts thereof exhibiting antimicrobial activity on a wide variety of microorganisms.

This technology utilizes the properties of reactive silanols and their ability to bond with a target surface. The reactive silanol will form a covalent bond with any surface containing oxygen, nitrogen or carbon in any form. For example hydroxides or oxides on the surfaces of metals (including stainless steel) will form a durable bond. In addition, silanol groups will homopolymerize via a condensation mechanism to form a durable, 3 dimensional crosslinked polymer matrix. The application is therefore very versatile and many types of surfaces may be treated, such as plastic, metal, fabric, tile, masonry, vinyl, wood, painted surfaces and human and animal skin, hair and nails.

The silanols are modified with biocidal adjuncts in the form of alkyl quaternary ammonium groups, so that when the silanols fix onto a surface, the active biocidal sites become fixed too. The films created are extremely thin, between 15 nm and 180 nm, and therefore the original physical properties of the surface are little affected.

Bacteria arriving on the surface encounter the hydrocarbon portion of the biocidal adjunct that may be assimilated into the cell without any disruption. However, contact with the positively charged nitrogen atom will unbalance the electrical equilibrium within the porin channels and on the outer protein layers such that the cells can no longer function correctly and the microbes will die without electron transfer. Therefore the positively charged nitrogen is immediately prepared to subsequently kill additional microbes. Since the kill is electrical and not poison, SQACs do not produce new, resistant strains of microbes such as MRSA.

The fixed nature of the SQAC biocide is important where toxicity, taint and other organoleptic aspects are of concern. This bactericidal surface treatment is not removed by normal cleaning procedures. In fact, it is important to maintain the normal cleaning regime in order to 'refresh' the biocidal surface. The thinness of the film enables application in areas where optical properties are important such as treatment of contact lenses. The technology has been used for treatment of bed sheets, hospital garments (Murray et al, 1988), curtains, floor and wall materials, air filtration systems, medical devices, bandages, surgical instruments and implants (Gottenbos et al, 2002). The technique has been used to prevent biofilm growth on catheters, stints, contact lenses and endotracheal tubes.

Hospital Acquired Infections are responsible for 100,000+ deaths per year in the United States alone. The SQAC technology is used to treat human skin where the SQAC covalently bonds to form a durable, antimicrobial barrier that lasts through many washes and provides up to 3 days of reduction or elimination of bacteria, viruses and fungi including the following non-limiting specific list of microbes (Peterson et al, 2003):
Bacteria:
Gram Positive Bacteria:
*Citrobacter freundii*
*Citrobacter diversus*
*Corynebacterium diptheriae*
*Diplococcus pneumoniae*
*Micrococcus* sp. (I)
*Micrococcus* sp. (II)
*Micrococcus* sp. (III)
*Mycobacterium* spp.
*Staphylococcus albus*
*Staphylococcus aureus*
*Staphylococcus citrens*
*Staphylococcus epidermidis*
*Streptococcus faecalis*
*Streptococcus pyogenes*
Gram Negative Bacteria:
*Acinetobacter calcoaceticus*
*Enterobacter aerogenes*

*Enterobacter aglomerans* (I)
*Enterobacter aglomerans* (II)
*Escherichia coli*
*Klebsiella pneumoniae*
*Nisseria gonorrhoeae*
*Proteus mirabilis*
*Proteus morganii*
*Proteus vulgaris*
*Providencia* spp.
*Pseudomonas*
*Pseudomonas aeruginosa*
*Pseudomonas fragi*
*Salmonella choleraesuis*
*Salmonella enteritidis*
*Salmonella gallinarum*
*Salmonella paratyphi* A
*Salmonella schottmuelleri*
*Salmonella typhimurium*
*Salmonella typhosa*
*Serratia marcescens*
*Shigella flexnerie* Type II
*Shigella sonnei*
*Virbrio cholerae*
Viruses:
Adenovirus Type IV
*Feline Pneumonitis*
Herpes Simplex Type I & II
HIV-1 (AIDS)
Influenza A (Japan)
Influenza A2 (Aichi)
Influenza A2 (Hong Kong)
Parinfluenza (Sendai)
Poliovirus
Reovirus
Respiratory Synctia
Fungi and Mold:
*Alternaria alternate*
*Asperigillus niger*
*Aureobasidium pullulans*
*Candida albicans*
*Cladosporium cladosporioides*
*Drechslera australiensis*
*Gliomastix cerealis*
*Microsporum audouinii*
*Monilia grisea*
*Phoma fimeti*
*Pithomyces chartarum*
*Scolecobasidium humicola*
*Trychophyton interdigitale*
*Trychophyton mentagrophytes*

The EPA's 2007 toxicity ruling on SQAC in the same EPA's Pesticide Docket #EPA-HQ-OPP-2007-0831 states "Upon reviewing the available toxicity information, the Agency has concluded that there are no endpoints of concern for repeated oral or dermal exposure to the trimethoxysilyl quats. This conclusion is based on low toxicity observed in acute, subchronic and developmental studies conducted with the trimethoxysilyl quat compounds. There are no concerns for carcinogenicity for the trimethoxysyl quats based on the results of the mutagenicity studies and the lack of any systemic toxicity being observed in the toxicity data base; therefore, no carcinogenic analysis is required."

The EPA's 2007 environmental fate ruling on SQAC as stated in EPA's Pesticide Docket # EPA-HQ-OPP-2007-0831 states "The Agency has conducted an environmental fate assessment dated Sep. 19, 2007 for the trimethoxysilyl quats. The hydrolysis data indicate that the trimethoxyslyl quats are soluble but not stable in water. Environmental fate studies for the trimethoxyslyl quats consist of only a hydrolysis study and it was concluded by the Agency that no further fate studies would be required because of the instability of the compounds and their formation of an insoluble silane degradate. The trimethoxysilyl quats are not expected to contaminate surface or ground water due to rapid degradation by hydrolysis."

For health, safety and economical reasons, it is most desirable to apply such antimicrobial SQACs from an aqueous medium, which may contain additives and components the purpose of which is to increase long term aqueous storage stability against homopolymerization of the hydrolyzed silanol groups causing viscosity increase and/or precipitation, provide scent and maintain solution clarity, improve performance and protect against aqueous mold growth.

Imparting long-term storage stablity, however, to the newly formed aqueous SQAC solution, is a major concern that directly impacts the use and marketability of such antimicrobial formulations. Experience has shown that even low aqueous concentrations are unstable, leading to the premature sedimentation of polysilsesquioxane-type polymers or to rapid increases in solution viscosity causing disruption to standard methods of coating applications. To improve shelf-life and storage stability, thus yielding a marketable formulation, many strategies have been implemented.

DESCRIPTION OF PRIOR ART

Some of the common approaches utilized in order to extend storage life of aqueous SQACs have been to introduce surfactant additives, to coordinate the free silanol ends with stabilizers such as simple sugars and other multiple hydroxyl group molecules, to coordinate/associate said quaternary organosilane hydrolysates with hydrophilic polymers, to incorporate non-aqueous solvents such as the toxic methanol and methyl or butyl cellosolve, to use alternative aqueous/organic systems, and to apply combinations thereof. In some cases, pH adjustments have been used to maximize the benefits imparted by a stabilizer. The implementation of such strategies has proved instrumental and necessary to yield marketable water-based formulations.

It is desirable to employ additives that will evaporate completely during the coating and curing operation thus allowing the generation of a high degree of homo polymer crosslinking of the silanol groups providing a highly water and solvent insoluble coating on the substrate. Non-volatile additives, especially hydrophilic additives, that retard polymerization of aqueous solutions may also retard this degree of crosslinking needed during the cure of the film, making this antimicrobial coating more susceptible to greater rate of loss in applications where water comes in frequent contact with the cured film. In addition, non-volatile additives that become part of the cured film will decrease the cationic charge density which may lead to inferior antimicrobial efficacy.

The following patents and patent applications teaching stabilization of aqueous SQACs are incorporated herein for reference. U.S. Pat. No. 6,376,696 and WO00/78770 outline a process to prepare a quaternary ammonium silane from tetradecyldimethylamine and 3-chloropropyltrimethoxysilane, in which the yield during quaternization is quantitative and the product is dissolved and stabilized in an aqueous solution containing methyl triglycol as active stabilizer, however this stabilizer both hydrophilic and non-volatile.

U.S. Pat. No. 3,560,385 outlines to a process to prepare a quaternary ammonium silane from octadecyldimethylamine and 3-chloropropyltrimethoxy silane in methyl cellosolve. The yield of quaternization is near quantitative and said product is easily dissolved and retained in water by virtue of methyl cellosolve, acting as active stabilizer, however methyl cellosolve is quite toxic and hydrophilic.

U.S. Pat. No. 6,613,755 outlines a process to dissolve methanolic solutions of quaternary amines in water, giving an overall very low concentration of the antimicrobial with respect to the final water/methanol solution. However, shipping such low concentrations is very uneconomical and methanol is toxic.

U.S. Pat. No. 6,632,805 and WO97/41729 relate to a process to prepare a quaternary ammonium silane from octadecyldimethylamine and 3-chloropropyltrimethoxysilane. In following a process, which implements pH control and the addition of an active stabilizer, a stable solution of the trioxaslylbicycloctyl intermediate species is obtained. Stabilizers included pentaerythritol, tris(hydroxymethyl) ethane, tris(hydroxymethyl)methane, and similar compounds. Such compounds, although good stabilizers for aqueous SQACs are hydrophilic and quite non-volatile and may be incorporated into the cured film and may reduce the charge density and antimicrobial efficacy as well as water resistance.

US20080181862 relates to the preparation of an antimicrobial polysiloxane. As part of this embodiment, a dimethylaminopropyl organosilane is quaternized using an alkyl halide and the ensuing product is solvated in methanol but not water, yielding large amounts of toxic methanol being released during cure.

US2010/0028462 relates to the preparation of a water-stable quaternary ammonium organosilane hydrolysate. Here, the key to retaining stability is the incorporation of a hydrophilic, non-ionic surfactant. Although good stability is obtained, such mixtures may foam badly during application and may require a post treatment wash to remove the surfactant since most non-ionic surfactants lack any volatility.

U.S. Pat. No. 4,842,766 relates to clear microemulsions of SQACs and water in wt ratios of 1/99 to 99/1 using a cosurfactant selected from a group having an HLB of >1. Specific examples are propylene glycol, ethylene glycol, pentanol, decanol, and glycerol. However, the concentrated SQAC needs to contain low levels methanol in order for the microemulsion to form.

U.S. Pat. No. 6,613,755 relates to stable aqueous solutions of SQACs in distilled or deionized water when measured conductively has an electrical resistance of at least 10 megohm per square centimeter with a purity level of 18 megohm per square centimeter being preferred. However, the authors admit the presence of dissolved impurities such as metal ions, metal salt and anionic species, particularly fluoride ions will greatly decrease the stability and shelf life of the aqueous formulations. Thus, any downstream contamination of this type will cause this unstabilized formulation to spoil.

The above patents and applications along with many others not referenced, demonstrate there is a clear and present need to discover a class of stabilizers having all of the following attributes:

1) Low Toxicity 2) Low Flammability 3) Excellent stabilization of aqueous SQACs 4) Pleasant scent 5) Volatlity (little or no incorporation of the stabilizer into the cured film) 6) Antimicrobial Activity 7) Obtained from a renewable resource Unexpectedly, a unique group of stabilizers has been discovered that satisfies all 7 of the above attributes needed to correct the shortcomings of previous inventions of this type. These unique stabilizers are certain naturally derived, renewable, phytochemical essential oils that have been proven to possess low toxicity, low flammability, excellent stabilization of aqueous SQACs, pleasant scent, good volatility, and demonstrate antimicrobial activity of their own.

BRIEF DESCRIPTION OF THE INVENTION

This instant invention is a process for the manufacture of water stabilized antimicrobial silanol quaternary ammonium compounds where the stabilizing agent is chosen from the collective group of essential oils and extracts that are commonly obtained by steam distillation or cold pressing of stems, bark, leaves, fruit, peels and flowers of various plant species throughout the world. Some of the preferred essential oils used in the instant invention are derived from leaves that are edible herbs. Other preferred essential oils are extracted from the peels of citrus fruits that are used as flavorings for food and beverages. This source of stabilizing agents is plentiful, renewable and generally considered to have low toxicity to humans and animals. The process of this invention teaches the manufacture of crystal clear, water stabilized SQAC microemulsions with essential oils that show little or no sign of $2^{nd}$ degree homopolymerization (viscosity increase) of $3^{rd}$ degree homopolymerization (polymer precipitation) when aged at room temperature for several months at SQAC assays that allow for good transportation economics and excellent utility in use when further diluted.

DETAILED DESCRIPTION OF THE INVENTION

For purposes of demonstrating the process of this invention, the follow SQAC compounds were selected as preferred examples from the general formula given above:

SQAC #1 3-(trimethoxysilyl) propyl-N-octadecyl-N,N-dimethyl ammonium chloride

SQAC #2 3-(trimethoxysilyl) propyl-N-tetradecyl-N,N-dimethyl ammonium chloride

SQAC #3 3-(triethoxysilyl) propyl-N-octadecyl-N,N-dimethyl ammonium chloride

SQAC #4 3-(trimethoxysilyl) propyl-N-didecyl-N,N-dimethyl ammonium chloride

SQAC #1 is commercially available from Indusco, Ltd in Greensboro, N.C. as Bioshield 7200 and is sold as a concentrated solution of the active ingredient in anhydrous methanol. A similar product is available from both Dow Corning and Microban International and others. Of the three selected SQAC compounds, SQAC #1 is the most preferred compound for demonstrating the process of this invention due to its high sales volume and popularity of use as an antimicrobial coating on a myriad of substrates.

The following, although illustrative of examples of antimicrobial phytochemical plant species whose essential oils and extracts that can be used in this invention, but is not meant to be an all-inclusive list:

*Jasonia candicans* (sesquiterpenes, lactones); *Polygonum flaccidum* (flavone and alpha santalene derivatives); *Acalypha wikesiana* (extracts); *Pavetta owariensis* (procyanidins); *Plectranthus hereroensis* (diterpenoids, diterpenes); Moss (Dicranin extract); *Cannabis sativa* (extract); *Gloiosiphonia* spp. (gloiosiphones); *Laminaceae* spp. (extract); *Securidaca* spp. (extract); *Veronia* spp. (extract); *Hyptis*

*umbrose* (umbrosone); *Asclepias syriaca* (milkweed extract); *Tagetes tenuifolia* (thiophene); *Calophyllum inophylloide* (flavonoids); *Tanacetum densum* (sesquiterpene lactones, triterpenoids); *Neorautanenia mitis* (extract); *Premna schimper* (diterpene); *Premna oligotricha* (sesquiterpenes); *Premna oligotricha* (diterpenes); *Jasonia candicans* (essential oils); *Visnea mocanera* (beta-sitosterol, triterpenic betulinic acid, ursolic acid, plantanic acid); *Asteraceae* spp. (terthiophenes and polyynes); *Petalostemum purpureum* (extract); *Camelia sinensis* (catechin); *Helichrysum picardii* (flavonoids); *Helichrysum italicum* (flavonoids); *Corydalis pallida* (protoberberine alkloids); *Shiraia bambusicola* (perylenequinones); *Fraxinum omus* (hydroxycoumarins); *Podocarpus nagi* (totarol and nortiterpene dilactones); *Heterotheca inuloides* (sesquiterpenoids); *Pelargonium* spp. (essential oils); *Piper sarmentosum* (phenylpropanoids); *Allium* spp. (extract); *Juniperus procera* (diterpenes); *Achillea conferta* (flavonoids, flavones, sesquiterpenoid lactones); *Magnolia virginiana* (lignans, neolignans); *Eucalyptus euglobal* (euglobal); *Armilaria mellea* (armilaric acid); *Dracena mannii* (spirostanol saponin); *Piper aduncum* (chromenes, prenylated benzoic acid); *Rhamnaceae* spp. (cyclopeptide alkaloids); *Buddleja globosa* (verbascoside); *Cephalocereus senilis* (phytoalexin aurone); *Salvia albocaerulea* (diterpene); *Gomphrena martiana* and *Gomphrena boliviana* (extracts); *Paepalanthus* spp. (vioxanthin); *Helichrysum stoechas* and *Helichrysum crispum* (extracts); *Achilea ptarmica* (trans-pinocarveyl hydroperoxides); *Dehaasia incrassata* (alkaloids); *Asteraceae* spp. (extracts); *Arctotis auriculate* (extracts); *Eriocephalus africanus* (extracts): *Felicia erigeroides* (extracts); *Hemerocallis fulva* (phytosterols, fatty acid esters); *Psoralea juncea* (plicatin B); *Pluchea symphytifolia* (caffeic acid esters); *Tovomitopsis psychotrifolia* (Vitamin E derivative), *Celosia argentea* (triterpenoid saponins and flavonoids); *Azadirachta indica* (tetranortriterpenoid, mahmoodin, protolimonoids, naheedin); *Moraceae* spp. (coumarins); *Hypericum erectum* (phloroglucinol derivatives); *Podospora appendiculate* (Appenolides A, B, & C, furanones); *Artemisia princeps* var. *orientalis, Artemisia capillaris, Artemisia mexicana* and *Artemisia scoparia* (extract); Paddy malt (mash extract); *Kigelia pinnata* (extract); *Acalypha wilkesiana* (extract); seaweeds, seagrass and lemongrass (essential oils); *Borreria latifolia, Borreria setidens, Hedyotis diffusa), Hedyotis nudicaulis, Morinda elliptica, Morinda umbellata, Sida rhombifolia,* and *Vitex ovata* (extracts); *Tabebuia impetiginosa, Achyrocline* spp., *Larrea divaricata, Rosa borboniana, Punica granatum, Psidium guineense, Lithrea temifolia* (extracts); *Lepechinia caulescens, Lepidium virginicum* and *Tanacetum parthenium* (extracts); *Talaromyces flavus* (extracts); *Daucus carota* (extract); *Flabellia petiolata, Caulerpa prolifera, Halimeda tuna, Corallina elongata, Lithophyllum lichenoides, Phyllophora crispa, Cystoseira* spp., *Halopteris* spp., *Codium* spp., *Valonia utricularis, Posidonia oceanica, Zostera nolti* and *Cymodocea nodosa* (extracts); *Centauraea orientalis, Diospyros khaki, Sida hermaphrodita, Forsythia intermedia, Scutellaria polydon, Eugenia malaccensis* and *Eugenia jambolana* (extracts); *Fritillaria* L. spp. (ebeinone, steroidal alkaloids); *Kigelia pinnata, Peperomia pellucida, Populus nigra, Populus balsamifera* and *Populus deltoides* (extracts); *Melaleuca altemifolia* (essential oil); *Elfvingia applanata* (naringenin); *Ficus sycomorus,* grapefruit seed, Garlic, Allicin, Peat, *Strophanthus hispidus, Secamone afzeli, Mitracarpus scaberi, Entada abyssinjca, Terminalia spinosa, Harrisonia abyssinica, Ximinea caffra, Azadirachta indica, Spilanthes mauritiana, Terminalia spinosa* (extracts); *Cyanobacteria* (ambigols A and B, tjipanazole); coffee (extract); *Sporochnus pedunculatus, Dalbergia melanozylon, Celastrus scandens, Juglans nigra, Kalmia latifolia, Pelargonium xhortorum, Rhus glabra* and *Lindera benzoin* (extracts); *Striga densiflora, Striga orobanchioides, Striga lutea, Pistacia lentiscus* L., *Mitracarpus villosus, Bixa orellana, Bridelia ferruginea, Alpinia katsumadai, Alpinia officinarum, Artemisia capillaris, Casia obtusifolia, Dendrobium monliforme, Epimedium grandiflorum, Glycyrrhiza glabra, Lithosperum erythrorhizon, Magnolia obovata, Morus bonbycis, Natopterygii incisium, Polygonum multiflorum, Prunus mume, Rheum palmatum, Ricinus communis, Sophora flavescens, Swertia japonica,* black pepper, rosemary, red pepper, *Isopyrum thalictroides, Calotropis procera, Chrysanthemum* spp., *Holarrhena antidysenterica, Lunularia crusiata, Dumertiera hirsuta, Exormotheca tuberifera,* and liverwort (extracts); *Flipendula ulmaria, Salix glauca, Usnea filipendula, Clkadina arbuscula* (salicylic compounds); *Tanacetum parthenium, Thymus capitatus,* and *Elfingia applanata* (extracts); *Fraxinus ornus* (hydroxycoumarins, esculin, esculetin, fraxin, and fraxetin); *Ziziphus nummularia,* LONGO VITAL, *Pelargonium* spp., *Scaevola sericea, Psychotria hawaiiensis, Pipturus albidis, Aleurites moluccana, Solanum niger, Piper methysticum, Barringtonia asiatica, Adansonia digitata, Harungana madagascariensis, Jacaranda mimosaefolia, Erythroxylum catauba, Bidens pilosa, Lemna minor, Potamogeton* spp., *Nasturtium officinale, Apium nodiflorum, Agaricus subrutilescens, Amanita virosa, Amanita pantherina, Lycoperdon perlatum, Psidium guajava, Averrhoa carambola, musa sapientum, Carica papaya, Passiflora edulis, Lansium domesticum* and *Baccaurea motleyana* (extracts); horse radish, celandine grass, bur marigold and yarrow grass (extracts); *Abuta grandifola, Cyperus articulatus, Gnaphalium spicatum, Pothomorphe peltata, Ficus sycomorus, Ficus Benjamina, Ficus bengalensis, Ficus religiosa, Alchornea cordifolia, Bridelia feruginea, Eucalyptus citriodora, Hymenocardia acida, Maprounea africana, Monachora arbuscula, Tedania ignis, Arenosciera* spp., *Amphimedon viridis, Polymastia janeirensis, Aplysina fulva, Pseudaxinella lunaecharta, Nelumbium speciosum* and *Mycale arenosa* (extracts); cloves (eugenol acetate and iso-eugenol); *Chrysthanemum boreale* (sesquiterpenoid lactones); *Eucalyptus globolus, Punica granatum, Bocconia arborea, Syzygium brazzavillense, Syzygium guineense, Carthamus tinctorius), Ginkgo biloba, Mosla chinensis, Salvia officinalis,* and *Cinnamomum cassia* (extracts); *Cryptolepis sanguinolenta* (alkaloids, cryptolepine); *Chelidonium majus* (alkaloids, berberine, coptisine); *Vitex agnus-castus* (extract); *Cladonia substellata* (usnic acid); *Fuligo septica, Tubifera microsperma* (extract); *Mundulea monantha, Tephrosia linearis* (flavonoids); *Lpomoea fistulosa* (extract); *Pimenta dioica* (essential oils); *Ratibida latipalearis, Teloxys graveolens, Dodonaea viscosa, Hypericum calycinum, Hyptis albida, Hyptis pectinata, Hyptis suaveolens* and *Hyptis verticillata* (extracts); *Asteriscus graveolones* (bisabolone hydroperoxides); *Derris scandens, Alnus rubra,* Araliaceae family (extracts); *Vinca rosea,* Australian tea tree oil, peppermint oil, sage oil, thyme oil, thymol, grapefruit oil, lemon oil, lime oil, orange oil, tangerine oil, cedarwood oil, pine oil and d-limonene, eugenol and *Thuja orientalis* (extracts); *Anacardium occidentale* (phenolic lipids); *Oidiodendron tenuissimum* (extract); *Acacia nilotica* and *Acacia famesiana* (polyphenol, tannin); *Teminalia alata* and *Mallotus phillipinensis* (extracts); *Piectranthus grandidentatus* (abientane diterpenoids); *Pumica granatum* and *Datura metel* (extracts); tea, *Agave lecheguilla, Chamaesyce hirta, Bac-*

*charis glutinosa* and *Larrea tridentata* (extracts); *Camelia sinensis* and *Euphorbia hirta* (theaflavin, polyphenon 60); *Tabemaemontana pandacaqui, Yucca shidigera, Hemistepa lyrata, Yougia japonica, Prunella vulgaris, Lamium amplexicaule, Juniperus chinensis, Ixeris dentata, Gnaphalium affine, Chelidonium majus, Spirea prunifolia, Erythronium japonicum, Taxus wallichiana, Ganoderma lucidum Drava nemorosa, Youngia capillaris, Equisetum arvense*, Australiam Lavender, Black Seed, Catuaba casca, Cineole, Damiana, *Dicranum scoparium*, Eucalyptus oil, Ginger, and Grape seed (extracts); Neem seed, bark, and leaf extract; Neem oil; New Zealand Manuka extract; *Nicotiana tabacum* extract; olive leaf extract; a-pinene and b-pinene extracts; Rhubarb root extract; *Syringa vulgaris* extract.

For purposes of demonstrating the process of this invention, preferred essential oils that have biocidal activity and form crystal clear microemulsions with aqueous SQACs are the essential oils of tea tree, peppermint, thyme, grapefruit, lemon, lime, orange, tangerine, cedarwood and pine and orange peel extract d-limonene. The process of the instant invention produces novel, crystal clear, viscosity stable, oil-in-water microemulsions using SQACs, phytochemical extracts or essential oils, and distilled or deionized water. Microemulsion technology has been in existence for many years. In fact many commercial microemulsion products are found in the marketplace including floor polishes and cleaners, personal care products, pesticide delivery systems, cutting oils and drug delivery systems. Microemulsions are crystal clear because the micellar particle size is too small to scatter visible light. The IUPAC definition of microemulsion is "a dispersion of water, oil and surfactant(s) that is an isotropic and thermodynamically stable system with dispersed domain diameter varying approximately from 1 to 100 nm, usually 10 to 50 nm." The aqueous phase may contain salts or other ingredients such as polar solvents, and the oil may be a complex mixture of organic compounds. In contrast to ordinary, white macroemulsions that usually require high shear conditions to form, microemulsions form upon simple mixing of the components.

Unexpectedly, the SQAC which not only is the active ingredient producing durable antimicrobial films when cured, also does double duty as the only required surfactant needed to form the microemulsion with phytochemical essential oils and extracts. Such microemulsions need only standard mixing requirements such as those found in low speed mixing vessels, not high shear equipment such as various types of high speed or high pressure homogenizers. These microemulsions have been developed on lab scale using only the shear of low speed magnetic stirring bar mixing.

It has been determined that when preparing these microemulsions, order of addition is quite important. The SQAC is first to be added to the mixing vessel as a concentrated solution in the reaction solvent, followed by adding the essential oil or extract which dissolves in the concentrated SQAC to form a low viscosity, easily mixable, clear solution. The addition of the essential oil or extract will lower the temperature at which partial insolubility of the SQAC occurs, similarly to what would be expected if more reaction solvent was added. Mixtures of SQAC and essential oil or extract have been stored at room temperature for several months and show no signs of precipitation, loss of activity, color change or their ability to form microemulsions when additional water is mixed in.

To accomplish the process of making a crystal clear, viscosity stable emulsion, all that is needed is the addition of distilled or deionized water to the SQAC/essential oil or extract solution that is under moderate agitation. Depending upon the type of SQAC and essential oil or extract being used, it was found that water heated above room temperature produces clear microemulsions more quickly. Preferred water temperature depends in part on the boiling point of the SQAC/essential oil/polar solvent mixture being treated based on safety considerations.

The rate of water addition is also dependent upon the components being used. Some systems allow water addition rates as rapid as less than one minute, while other systems require a water addition rate that will maintain a clear microemulsion mixing in the vessel. Microemulsion systems will maintain this clear appearance throughout the water addition process. This is the "best mode" for carrying out the process of this invention. If any turbidity of the mixing vessel contents occurs, there is a good chance a microemulsion will not be formed to completion resulting in less than crystal clarity of the final dispersion. Cloudy microemulsions may be repaired to form clear microemulsions by post heating the fully diluted microemulsion, then stopping the agitation and allowing the microemulsion to slowly cool to room temperature.

Although most of the aging stability studies were performed on an economically shippable 6.0% SQAC concentration, further dilution with water produced crystal clear, stable microemulsions all the way down to <0.01% SQAC concentration. Stability against precipitation remained excellent through this dilution range.

EXAMPLES

The present inventions can best be understood after a review of the following non-limiting examples:

Example 1

Into an 8 oz. glass jar was weighed 16.67 g of Bioshield 7200 (72% active SQAC) followed by 3.60 g of tea tree essential oil and stirred on a magnetic stirring plate until the two components were clear and uniform (~1 min). With continued moderate stirring, 179.73 g of distilled water at a temperature of 35 C to 45 C was rapidly poured into the jar. Stirring was continued as the transparent concentrate slowly dissolved in the water to form a crystal clear microemulsion of tea tree oil in a 6.0% active Bioshield continuous phase. Brookfield viscosity of the freshly prepared microemulsion was measured at 10 cPs at 25 C and the pH was measured at 3.7 without any adjustment. The jar was sealed and placed in a 25 C static oven and analyzed weekly for both viscosity increase (linear condensation polymerization) and development of insoluble precipitation (3 dimensional crosslinking) as measured by Hach Ratio Turbidimetry. After 3 months aging at 25 C this sample was measured at 40 cPs and 5 Nephelos Turbidity Units (NTU).

Example 2

Into an 8 oz. glass jar was weighed 16.67 g of Bioshield 7200 (72% active SQAC) followed by 2.22 g of peppermint essential oil and stirred on a magnetic stirring plate until the two components were clear and uniform (~1 min). With continued moderate stirring, 181.11 g of distilled water at a temperature of 35 C to 45 C was rapidly poured into the jar. Stirring was continued as the transparent concentrate slowly dissolved in the water to form a crystal clear microemulsion of peppermint oil in a 6.0% active Bioshield continuous phase. Brookfield viscosity of the freshly prepared microemulsion was measured at 10 cPs at 25 C and the pH was measured at 3.7 without any adjustment. The jar was sealed and placed in a 25 C static oven and analyzed weekly for both viscosity increase (linear condensation polymerization) and development of insoluble precipitation (3 dimensional crosslinking) as measured by Hach Ratio Turbidimetry. After 4 months aging at 25 C this sample was measured at 20 cPs and 33 NTU.

Example 3

Into an 8 oz. glass jar was weighed 16.67 g of Bioshield 7200 (72% active SQAC) followed by 2.18 g of Thyme essential oil (*T. vulgaris*) and stirred on a magnetic stirring plate until the two components were clear and uniform (~1 min). With continued moderate stirring, 181.15 g of distilled water at a temperature of 35 C to 45 C was rapidly poured into the jar. Stirring was continued as the transparent concentrate slowly dissolved in the water to form a crystal clear microemulsion of thyme oil in a 6.0% active Bioshield continuous phase. Brookfield viscosity of the freshly prepared microemulsion was measured at 10 cPs at 25 C and the pH was measured at 3.7 without any adjustment. The jar was sealed and placed in a 25 C static oven and analyzed weekly for both viscosity increase (linear condensation polymerization) and development of insoluble precipitation (3 dimensional crosslinking) as measured by Hach Ratio Turbidimetry. After 4 months aging at 25 C this sample was measured at 24 cPs and 30 NTU.

Example 4

Into an 8 oz. glass jar was weighed 16.67 g of Bioshield 7200 (72% active SQAC) followed by 3.60 g of grapefruit essential oil and stirred on a magnetic stirring plate until the two components were clear and uniform (~1 min). With continued moderate stirring, 179.73 g of distilled water at a temperature of 35 C to 45 C was rapidly poured into the jar. Stirring was continued as the transparent concentrate slowly dissolved in the water to form a crystal clear microemulsion of grapefruit oil in a 6.0% active Bioshield continuous phase. Brookfield viscosity of the freshly prepared microemulsion was measured at 10 cPs at 25 C and the pH was measured at 3.7 without any adjustment. The jar was sealed and placed in a 25 C static oven and analyzed weekly for both viscosity increase (linear condensation polymerization) and development of insoluble precipitation (3 dimensional crosslinking) as measured by Hach Ratio Turbidimetry. After 4 months aging at 25 C this sample was measured at 32 cPs and 8 NTU.

Example 5

Into an 8 oz. glass jar was weighed 16.67 g of Bioshield 7200 (72% active SQAC) followed by 3.60 g of orange essential oil and stirred on a magnetic stirring plate until the two components were clear and uniform (~1 min). With continued moderate stirring, 179.73 g of distilled water at a temperature of 35 C to 45 C was rapidly poured into the jar. Stirring was continued as the transparent concentrate slowly dissolved in the water to form a crystal clear microemulsion of orange oil in a 6.0% active Bioshield continuous phase. Brookfield viscosity of the freshly prepared microemulsion was measured at 10 cPs at 25 C and the pH was measured at 3.7 without any adjustment. The jar was sealed and placed in a 25 C static oven and analyzed weekly for both viscosity increase (linear condensation polymerization) and development of insoluble precipitation (3 dimensional crosslinking) as measured by Hach Ratio Turbidimetry. After 3 months aging at 25 C this sample was measured at 22 cPs and 5 NTU.

Example 6

Into an 8 oz. glass jar was weighed 16.67 g of Bioshield 7200 (72% active SQAC) followed by 3.60 g of lime essential oil and stirred on a magnetic stirring plate until the two components were clear and uniform (~1 min). With continued moderate stirring, 179.73 g of distilled water at a temperature of 35 C to 45 C was rapidly poured into the jar. Stirring was continued as the transparent concentrate slowly dissolved in the water to form a crystal clear microemulsion of lime oil in a 6.0% active Bioshield continuous phase. Brookfield viscosity of the freshly prepared microemulsion was measured at 10 cPs at 25 C and the pH was measured at 3.7 without any adjustment. The jar was sealed and placed in a 25 C static oven and analyzed weekly for both viscosity increase (linear condensation polymerization) and development of insoluble precipitation (3 dimensional crosslinking) as measured by Hach Ratio Turbidimetry. After 4 months aging at 25 C this sample was measured at 36 cPs and 12 NTU.

Example 7

Into an 8 oz. glass jar was weighed 16.67 g of Bioshield 7200 (72% active SQAC) followed by 3.60 g of tangerine essential oil and stirred on a magnetic stirring plate until the two components were clear and uniform (~1 min). With continued moderate stirring, 179.73 g of distilled water at a temperature of 35 C to 45 C was rapidly poured into the jar. Stirring was continued as the transparent concentrate slowly dissolved in the water to form a crystal clear microemulsion of tangerine oil in a 6.0% active Bioshield continuous phase. Brookfield viscosity of the freshly prepared microemulsion was measured at 10 cPs at 25 C and the pH was measured at 3.7 without any adjustment. The jar was sealed and placed in a 25 C static oven and analyzed weekly for both viscosity increase (linear condensation polymerization) and development of insoluble precipitation (3 dimensional crosslinking) as measured by Hach Ratio Turbidimetry. After 4 months aging at 25 C this sample was measured at 32 cPs and 12 Nephelos Turbidity Units (NTU).

Example 8

Into an 8 oz. glass jar was weighed 16.67 g of Bioshield 7200 (72% active SQAC) followed by 3.60 g of lemon essential oil and stirred on a magnetic stirring plate until the two components were clear and uniform (~1 min). With continued moderate stirring, 179.73 g of distilled water at a temperature of 35 C to 45 C was rapidly poured into the jar. Stirring was continued as the transparent concentrate slowly dissolved in the water to form a crystal clear microemulsion of lemon oil in a 6.0% active Bioshield continuous phase. Brookfield viscosity of the freshly prepared microemulsion was measured at 10 cPs at 25 C and the pH was measured at 3.7 without any adjustment. The jar was sealed and placed in a 25 C static oven and analyzed weekly for both viscosity increase (linear condensation polymerization) and development of insoluble precipitation (3 dimensional crosslinking) as measured by Hach Ratio Turbidimetry. After 4 months aging at 25 C this sample was measured at 30 cPs and 7 Nephelos Turbidity Units (NTU).

Example 9

Into an 8 oz. glass jar was weighed 16.67 g of Bioshield 7200 (72% active SQAC) followed by 3.60 g of pine essential oil and stirred on a magnetic stirring plate until the two components were clear and uniform (~1 min). With continued moderate stirring, 179.73 g of distilled water at a temperature of 35 C to 45 C was rapidly poured into the jar. Stirring was continued as the transparent concentrate slowly dissolved in the water to form a crystal clear microemulsion of pine oil in a 6.0% active Bioshield continuous phase. Brookfield viscosity of the freshly prepared microemulsion was measured at 10 cPs at 25 C and the pH was measured at 3.7 without any adjustment. The jar was sealed and placed in a 25 C static oven and analyzed weekly for both viscosity increase (linear condensation polymerization) and development of insoluble precipitation (3 dimensional crosslinking) as measured by Hach Ratio Turbidimetry. After 4 months aging at 25 C this sample was measured at 30 cPs and 9 NTU.

Example 10

Into an 8 oz. glass jar was weighed 16.67 g of Bioshield 7200 (72% active SQAC) followed by 3.60 g of cedarwood essential oil and stirred on a magnetic stirring plate until the two components were clear and uniform (~1 min). With continued moderate stirring, 179.73 g of distilled water at a temperature of 35 C to 45 C was rapidly poured into the jar. Stirring was continued as the transparent concentrate slowly dissolved in the water to form a crystal clear microemulsion of cedarwood oil in a 6.0% active Bioshield continuous phase. Brookfield viscosity of the freshly prepared microemulsion was measured at 10 cPs at 25 C and the pH was measured at 3.7 without any adjustment. The jar was sealed and placed in a 25 C static oven and analyzed weekly for both viscosity increase (linear condensation polymerization) and development of insoluble precipitation (3 dimensional crosslinking) as measured by Hach Ratio Turbidimetry. After 4 months aging at 25 C this sample was measured at 8 cPs and 4 NTU.

Example 11

Into an 8 oz. glass jar was weighed 16.67 g of Bioshield 7200 (72% active SQAC) followed by 3.60 g of d-limonene (orange peel extract) and stirred on a magnetic stirring plate until the two components were clear and uniform (~1 min). With continued moderate stirring, 179.73 g of distilled water at a temperature of 35 C to 45 C was rapidly poured into the jar. Stirring was continued as the transparent concentrate slowly dissolved in the water to form a crystal clear microemulsion of d-limonene oil in a 6.0% active Bioshield continuous phase. Brookfield viscosity of the freshly prepared microemulsion was measured at 10 cPs at 25 C and the pH was measured at 3.7 without any adjustment. The jar was sealed and placed in a 25 C static oven and analyzed weekly for both viscosity increase (linear condensation polymerization) and development of insoluble precipitation (3 dimensional crosslinking) as measured by Hach Ratio Turbidimetry. After 6 months aging at 25 C this sample was measured at 32 cPs and 8 NTU. A further dilution of the stabilized 6% solution down to 0.75% active SQAC measured 3 NTU after 4 months aging at 25 C.

Comparative Example 12

Into an 8 oz. glass jar was weighed 16.67 g of Bioshield 7200 (72% active SQAC) followed by NO essential oil or extract. With moderate stirring, 183.33 g of distilled water at a temperature of 35 C to 45 C was rapidly poured into the jar. Stirring was continued as the transparent concentrate slowly dissolved in the water to form a crystal clear solution of a 6.0% active Bioshield. Brookfield viscosity of the freshly prepared solution was measured at 10 cPs at 25 C and the pH was measured at 3.6 without any adjustment. The jar was sealed and placed in a 25 C static oven and analyzed daly for both viscosity increase (linear condensation polymerization) and development of insoluble precipitation (3 dimensional crosslinking) as measured by Hach Ratio Turbidimetry. After 13 days aging at 25 C this sample was measured at 630 cPs and 100 NTU, exceeding both storage stability limits set at 50 cPs max viscosity and 40 NTU max clarity for these parameters.

While the invention has been described with respect to specific examples, variations and modifications may be made without departing from the spirit and scope of the invention. Such variations and modifications are to be considered within the purview and scope of the invention as defined by the appended claims.

I claim:

1. A method of utilizing a stabilized solution containing a silanol quaternary ammonium compound (SQAC) to reduce or eliminate microorganisms on a surface comprising:
    mixing an anhydrous SQAC defined as 3-(trimethoxysilyl) propyl-N-octadecyl-N,N-dimethyl ammonium chloride with cedarwood oil to form a solution,
    diluting the solution to a desired aqueous concentration with demineralized water,
    producing an optically clear microemulsion that is stabilized from premature polymerization, and
    applying the microemulsion to a surface, allowing it to dry and cure to form a durable, antimicrobial coating to eliminate or inhibit the growth of microorganisms.

2. The method of claim 1 wherein one or more additional anhydrous SQACs are selected from a group consisting of 3-(trimethoxysilyl) propyl-N-tetradecyl-N,N-dimethyl ammonium chloride, 3-(triethoxysilyl) propyl-N-octadecyl-N N-dimethyl ammonium chloride, and 3-(trimethoxysilyl) propyl-N-didecyl-N,N-dimethyl ammonium chloride and mixed to produce the optically clear, stable, antimicrobial microemulsion.

3. The method of claim 1 comprising the steps of;
    premixing the concentrated SQAC and the essential oil or extract to form a concentrated solution before adding demineralized water to form the alcohol-free optically clear, water stable, antimicrobial microemulsion without need for high intensity mixing,
    wherein a volume of the demineralized water is added to the concentrated solution of SQAC and essential oil or extract to form an alcohol-free, optically clear, stable microemulsion containing 1% to 8% active SQAC.

4. The method of claim 1 wherein the step of diluting the mixture with demineralized water further comprises diluting the microemulsion with a volume of water sufficient to produce an alcohol-free optically clear, stable, oil-in-water microemulsion containing 0.01% to 1.0% active SQAC.

5. The method of claim 1 further comprising the step of adding additional compounds to the microemulsion, the additional compounds selected from a group comprising cationic and non-ionic antimicrobials and surfactants, skin moisturizers, buffers, colorants, thickeners, preservatives, and perfumes.

6. The method of claim 5 wherein the step of applying a surface coating of the microemulsion further comprises;
dispensing the microemulsion in the form of a liquid, spray, foam, or gel, coating the surface, allowing it to dry and cure, forming a durable, polymeric antimicrobial coating covalently bonded to the surface, and
reducing or eliminating microorganisms for up to 72 hours.

7. A method of utilizing a stabilized solution containing a silanol quaternary ammonium compound (SQAC) to reduce or eliminate microorganisms on a surface of animal or human skin, hair and nails comprising;
mixing an anhydrous SQAC defined as 3-(trimethoxysilyl) propyl-N-octadecyl-N,N-dimethyl ammonium chloride with cedarwood oil to form a solution,
diluting the solution to a desired aqueous concentration with demineralized water, producing a mixture defining an alcohol-free, optically clear microemulsion that is stabilized from premature polymerization,
applying the microemulsion to the surface of animal or human skin, haft and nails, and
curing to form a durable polymeric antimicrobial coating covalently bonded to eliminate or inhibit the growth of microorganisms without added alcohol.

8. The method of claim 7 one or more additional anhydrous SQACs are selected from a group consisting of 3-(trimethoxysilyl) propyl-N-tetradecyl-N,N-dimethyl ammonium chloride, 3-(triethoxysilyl) propyl-N-octadecyl-N,N-dimethyl ammonium chloride, and 3-(trimethoxysilyl) propyl-N-didecyl-N,N-dimethyl ammonium chloride and mixed to produce the optically clear, stable, antimicrobial microemulsion.

9. The method of claim 7 comprising the steps of;
premixing the concentrated SQAC and the essential oil or extract to form a solution before adding demineralized water to form an alcohol-free, optically clear, stable, antimicrobial microemulsion without need for high intensity mixing,
wherein a volume of the demineralized water is added to the concentrated solution of SQAC and essential oil or extract to form an alcohol-free, stable microemulsion containing 1% to 8% active SQAC.

10. The method of claim 7 wherein the step of diluting the mixture with demineralized water further comprises diluting the microemulsion with a volume of water sufficient to produce an alcohol-free, stable, oil-in-water microemulsion containing 0.01% to 1.0% active SQAC.

11. The method of claim 10 wherein the step of applying a surface coating of the microemulsion further comprises;
dispensing the microemulsion in the form of a liquid, spray, foam, or gel, coating the surface, and
curing to form a durable, polymeric antimicrobial coating covalently bonded to the animal or human hair, skin and nails and reducing or eliminating microorganisms for up to 72 hours.

12. The method of claim 11 wherein the microorganisms being reduced or eliminated are selected from bacteria, viruses, fungi, mold, mildew, yeast and spores and mixtures thereof.

* * * * *

UNITED STATES PATENT AND TRADEMARK OFFICE
CERTIFICATE OF CORRECTION

PATENT NO. : 9,744,120 B2
APPLICATION NO. : 14/724364
DATED : August 29, 2017
INVENTOR(S) : Dennis Victor Neigel Page 1 of 1

It is certified that error appears in the above-identified patent and that said Letters Patent is hereby corrected as shown below:

In the Claims

In Claim 2, Column 14, Lines 46-47 the word:
"3-(trimethoxysilyl) propyl-N-didecyl-N,N-dimethyl ammonium chloride"
Is corrected to read as:
3-(trimethoxysilyl) propyl-N-dodecyl-N,N-dimethyl ammonium chloride In Claim 8, Column 15, Line 32 through Column 16, Line 1, the word:
"3-(trimethoxysilyl) propyl-N-didecyl-N,N-dimethyl ammonium chloride"
Is corrected to read as:
3-(trimethoxysilyl) propyl-N-dodecyl-N,N-dimethyl ammonium chloride Signed and Sealed this
Eighteenth Day of May, 2021

Drew Hirshfeld
*Performing the Functions and Duties of the
Under Secretary of Commerce for Intellectual Property and
Director of the United States Patent and Trademark Office*